(12) United States Patent
Miyake et al.

(10) Patent No.: US 6,495,603 B1
(45) Date of Patent: Dec. 17, 2002

(54) ANTI-INFLAMMATORY EYE DROP

(75) Inventors: Kensaku Miyake, Nagoya; Yoshihiro Tsuriya, Tokyo; Hiroko Yageta, Tokyo; Hidekazu Suzuki, Tokyo; Yoshihiro Toyoda, Tokyo, all of (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/712,172

(22) Filed: Nov. 15, 2000

Related U.S. Application Data

(63) Continuation of application No. PCT/JP99/02522, filed on May 14, 1999.

(30) Foreign Application Priority Data

May 15, 1998 (JP) .......................................... 10-150788
Mar. 5, 1999 (JP) .......................................... 11-058173

(51) Int. Cl.$^7$ .............................................. A61K 31/18
(52) U.S. Cl. ..................................... 514/601; 514/912
(58) Field of Search ................................. 514/601, 912

(56) References Cited

U.S. PATENT DOCUMENTS 5,990,148 A * 11/1999 Isakson et al. .............. 514/406

* cited by examiner

*Primary Examiner*—Zohreh Fay

(57) ABSTRACT

The present invention relates to an anti-inflammatory eye drop comprising a drug selectively inhibiting COX-2, selected from the group consisting of etodolac, N-(2-(cyclohexyloxy)-4-nitrophenyl) methane-sulfonamide and meloxicam, which only slightly damages corneal epithelium and conjunctiva and which is excellent in the anti-inflammatory effect.

7 Claims, 2 Drawing Sheets

*P<0.05, ***P<0.001 (Dunnett's Multiple Comparison)

ANTI-INFLAMMATORY EYE DROP

This application is a continuation of PCT/JP99/02522, filed May, 14, 1999.

TECHNICAL FIELD

The present invention relates to a therapeutic agent for treating inflammatory diseases of eyes in which prostaglandin serves as a mediator of inflammation and more specifically to an eye drop for preventing and treating anterior ophthalmic inflammatory diseases observed, for instance, after the operation of cataract.

BACKGROUND ART

A non-steroid anti-inflammatory agent such as those containing sodium diclofenac, which shows its anti-inflammatory effect through the inhibition of the biosynthesis of prostaglandin as a mediator of the inflammation, is used not only for the treatment of inflammatory diseases by oral administration, but also for treating a variety of inflammatory diseases through local administration. In addition, it has also widely been used, in the form of an eye drop as a locally administered drug, for treating ophthalmic inflammatory diseases, in particular, anterior ophthalmic inflammatory symptoms after the operation of cataract and complications observed during and after the operation.

On the other hand, such a non-steroid anti-inflammatory eye drop is excellent in the anti-inflammatory action, but there has clinically been pointed out the occurrence of a side effect such as disorders of corneal epithelium at a frequency of about 1.6% (see a document attached to a medicine manufactured and sold by Wakamoto Pharmaceutical Co., Ltd., 1996). In other words, there has been desired for the development of a non-steroid anti-inflammatory eye drop, which is not accompanied with a high probability of causing disorders of corneal epithelium as a side effect.

As a result of the recent progress in researches, there have been pointed out, as sites of action of the non-steroid anti-inflammatory agent, inhibition of two enzymes, i.e., cyclooxygenase-1 (hereunder referred to as "COX-1") and cyclooxygenase-2 (hereunder referred to as "COX-2"). It has been recognized that COX-1 serves to protect cells, while COX-2 is an enzyme involved in the inflammation. For this reason, there has been desired for the development of an anti-inflammatory agent, which can selectively inhibit COX-2 and has a low possibility of causing disorders of cells. The development of gastric ulcer as a side effect of a systemically administered anti-inflammatory agent has been studied in detail from such a standpoint discussed above. As a result, the roles of COX-1 and COX-2 have almost completely be elucidated and it has also been proved that the inhibition of COX-1 is involved in the development of gastric ulcer.

As has been described above, the mechanism of the action of these anti-inflammatory agents in the gastric ulcer has already been elucidated, but it has not yet been clear whether the disorders of corneal epithelium is caused by the same mechanism of action as that for the gastric ulcer or not. There has thus been desired for the development of a drug, which permits the distinct discrimination of the roles of COX-1 and COX-2 in such disorders of corneal epithelium and ophthalmic inflammatory diseases. Masferrer, JL et al. (Surv. Ophthalmol., 1997, 41 (suppl. 2):S35–40) reports that the anterior ophthalmic inflammation can be suppressed by a COX-2 inhibitor, but this article does not include any disclosure concerning the disorders of corneal epithelium. Miyake, K. (Clinical Ophthalmologists' Reports, 1997, 51(11):190–191) suggests that the use of a selective COX-2-inhibitor can relieve disorders of corneal epithelium, but the article does not include any specific disclosure concerning means for solving the same.

DISCLOSURE OF THE INVENTION

The inventors of this invention have used a drug, which selectively inhibits COX-2, among non-steroid anti-inflammatory drugs as an eye drop, have investigated the effect thereof on anterior ophthalmic inflammatory diseases and disorder of ophthalmic cells and thus have completed the present invention.

More specifically, the present invention relates to an anti-inflammatory eye drop containing, as an effective component, a drug having high COX-2 selectivity. The inventors of this invention have tried to inspect compounds having COX-1 and COX-2 selectivity for an anti-inflammatory effect in vivo and an ability of damaging cells in vitro and as a result, have found that an anti-inflammatory eye drop containing, as an effective component, a drug having high COX-2 selectivity is excellent in the anti-inflammatory effect and in the alleviation of the cell-damage. Accordingly, it is an object of the present invention to provide an anti-inflammatory agent, which can alleviate any damage of cells such as corneal epithelial cells and conjunctival cells and an eye drop, which does not cause severe disorders of corneal epithelium.

BEST MODE FOR CARRYING OUT THE INVENTION

Figure 1:
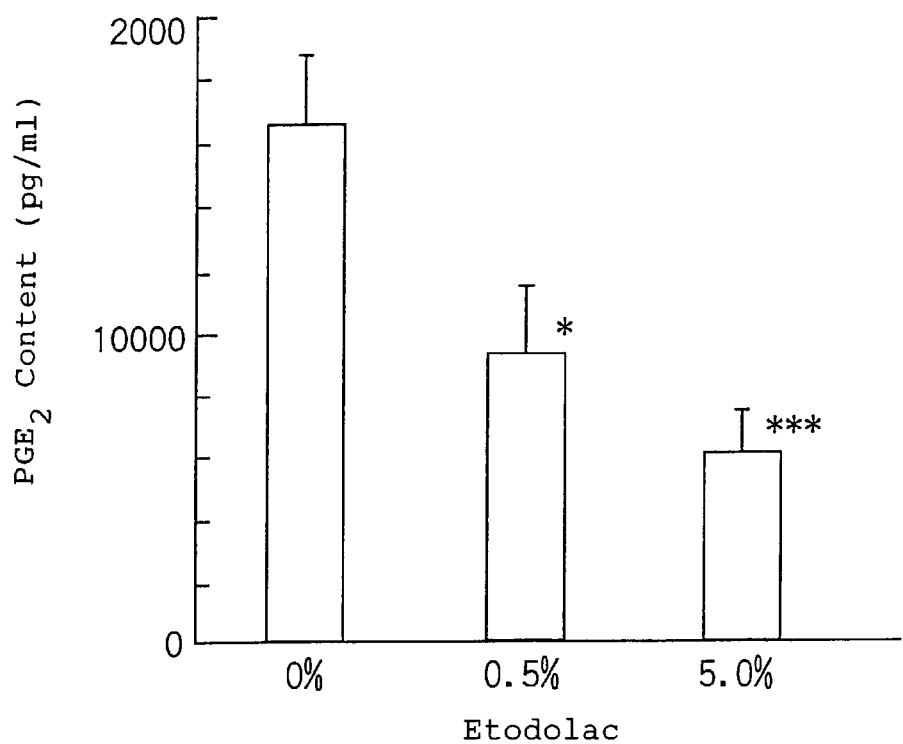
FIG. 1 is a graph showing the effect of etodolac on the $PGE_2$ content, which is increased by the anterior chamber puncture.

Preferred examples of non-steroid anti-inflammatory drugs having high COX-2 selectivity and used in the eye drop of the present invention are etodolac (1,8-diethyl-1,3,4,9-tetrahydropyrano [3,4-b] indole-1-acetic acid), N-(2-(cyclohexyloxy)-4-nitrophenyl) methanesulfonamide (NS-398) and meloxicam (4-hydroxy-2-methyl-N-(5-methyl-2-thiazolyl)-2H-1,2-benzo-thiazine-3-carboxamide 1,1-dioxide).

The eye drop of the present invention is desirably a sterilized pharmaceutical preparation, the preparations containing etodolac or NS-398 may comprise castor oil, sesame oil or other surfactants as a solubilizing agent and these effective components may be incorporated into ointments.

Meloxicam is also a drug having high COX-2 selectivity and is characterized in that it is highly water-soluble as compared with the foregoing drugs. Therefore, this drug can be used in an aqueous eye drop and may likewise be used in the form of an ointment.

The preferred concentration of such a drug used for treating inflammatory diseases ranges from 0.1% to 1% for meloxicam as an aqueous pharmaceutical preparation and 0.5% to 5% for an oily pharmaceutical preparation containing, for instance, etodolac or N-(2-(cyclohexyloxy)-4-nitrophenyl) methanesulfonamide. The effects of these drugs are confirmed by the inflammation model test.

In respect of the possibility of damaging cells, any drug having COX-2 selectivity shows low probability of damaging corneal epithelial cells and conjunctival cells. In particular, when exposing cells to the drugs for a long period of time, it has been clear that these drugs hardly cause disorders of corneal epithelium.

As has been described above, the present invention has, for the first time, provided an eye drop, which hardly damages cells such as corneal epithelial cells or conjunctival cells, in particular, an eye drop containing a selective COX-2 inhibitor, which shows high anti-inflammatory effect without causing any severe disorders of corneal epithelium.

The present invention will further be described in more detail with reference to the following working Examples and Test Examples.

EXAMPLE 1

| | |
|---|---|
| Etodolac | 5 g |
| Propyl p-Oxybenzoate | 0.01 g |
| Methyl p-Oxybenzoate | 0.05 g |
| Castor Oil | to 100 ml |

To 80 ml of castor oil, there were added propyl p-oxybenzoate and methyl p-oxybenzoate to thus dissolve them in the castor oil, then castor oil was further added to give a total volume of 100 ml and the resulting solution was sterilized by filtration to give an eye drop according to the present invention.

EXAMPLE 2

| | |
|---|---|
| N-(2-(cyclohexyloxy)-4-nitrophenyl) methanesulfonamide | 5 g |
| Propyl p-Oxybenzoate | 0.01 g |
| Methyl p-Oxybenzoate | 0.05 g |
| Castor Oil | to 100 ml |

To 80 ml of castor oil, there were added N-(2-(cyclohexyloxy)-4-nitrophenyl) methanesulfonamide, propyl p-Oxybenzoate and methyl p-oxybenzoate to thus dissolve them in the castor oil, then castor oil was further added to give a total volume of 100 ml and the resulting solution was sterilized by filtration to give an eye drop according to the present invention.

EXAMPLE 3

| | |
|---|---|
| Meloxicam | 0.5 g |
| Tween-80 | 0.5 g |
| Methyl Cellulose | 0.5 g |
| Boric Acid | 0.1 g |
| EDTA | 0.005 g |
| Benzalkonium Chloride | 0.005 g |
| 0.1 N HCl/0.1 N NaOH (an amount required for adjusting the pH to 7.2) | |
| Purified Water | to 100 ml |

To 80 ml of purified water, there were added meloxicam, Tween-80 (Polysorbate-80), methyl cellulose, boric acid, EDTA and benzalkonium chloride to thus dissolve these components in water. The pH value of the resulting solution was adjusted to 7.2 by the addition of 0.1N HCl or 0.1N NaOH and purified water was further added to the solution to give a total volume of 100 ml. The resulting solution was sterilized by filtration to give an eye drop of the present invention.

The method of using the eye drop of the present invention and the volume thereof to be administered may vary depending on, for instance, the symptoms of patients and age thereof, but the eye drop is in general dropped in the eyes in a dose of 1 to 2 drops over one to 6 times per day. Test Example 1

Effect of Eye Drop on Inflammation in Anterior of White Rabbit

In this Test Example, there were used Japanese white rabbits (available from Japan Medical Animal Source Laboratory) each having a body weight ranging from 1.8 to 2.4 kg and they were divided into groups each consisting of 6 to 7 animals.

After administration of 250 U/kg of heparin (available from Takeda Chemical Industries, Ltd.) to these rabbits through the ear veins thereof, a test substance was dropped in the both eyes in an amount of about 60 $\mu$l. After 45 minutes from the dropping of the substance in the eyes, these animals were locally anesthetized with benoxil eye drop (available from Santen Pharmaceutical Co., Ltd.) and then whole of the anterior chamber fluid was collected using a 27G injection needle. This anterior chamber fluid was defined to be a primary aqueous humor. After 90 minutes from the collection of the aqueous humor, the rabbits were killed by anesthetization with an excess of pentobarbital sodium and the aqueous humor was again collected. This anterior chamber fluid was defined to be a secondary aqueous humor.

The concentration of prostaglandin $E_2$ (hereunder referred to as "$PGE_2$") and the amount of proteins present in the collected secondary aqueous humor were determined and they were used as indications of inflammation. After pretreatment of 100 $\mu$l of the aqueous humor using a Bond Elute $C_{18}$ column, the concentration of $PGE_2$ was determined using Biotrack $PGE_2$ EIA system (available from Amersham Company). On the other hand, the amount of proteins was determined according to the Lowry method using bovine serum albumin (available from Nakarai Co., Ltd.) as a reference protein.

Etodolac as a test substance was dissolved in castor oil specified in the pharmacopoeia to concentrations of 0.5% and 5%. Meloxicam was diluted with physiological saline prior to use.

Figure 2:
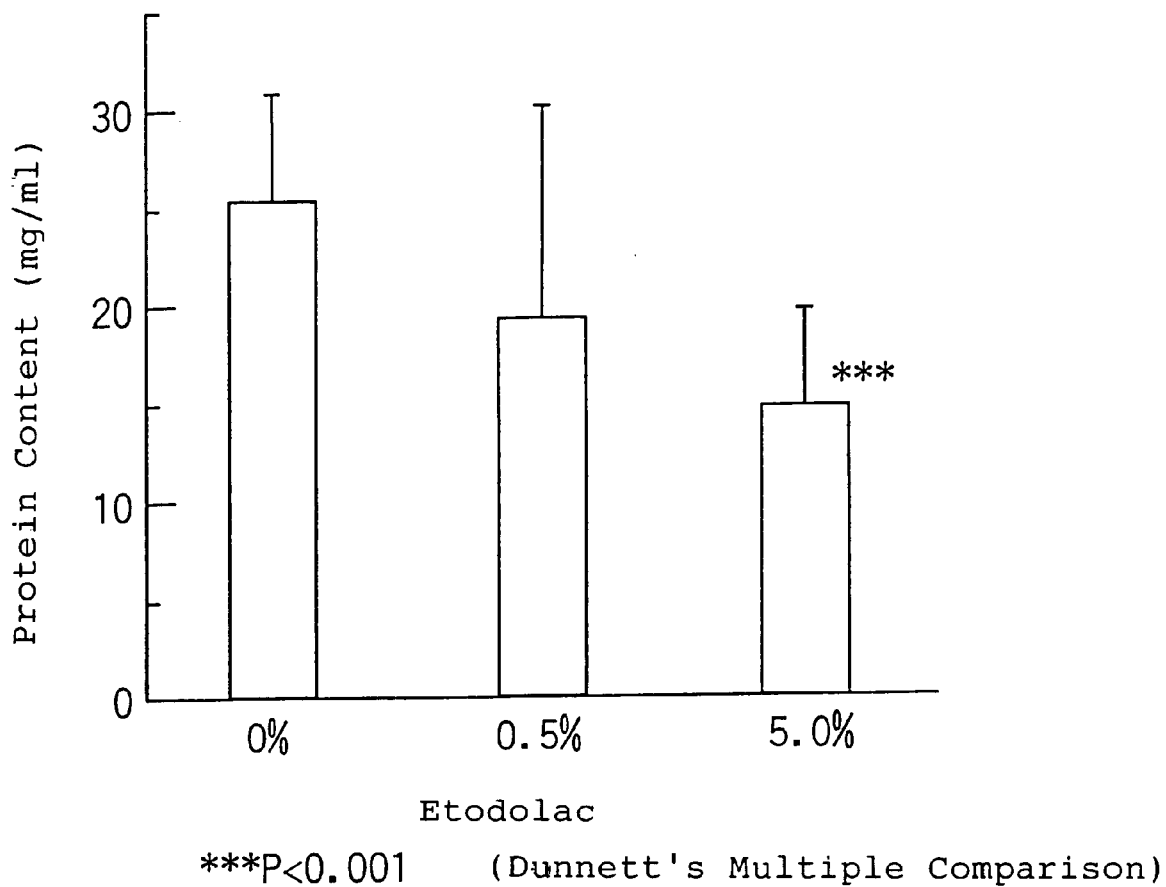
FIG. 2 is a graph showing the effect of etodolac on the protein content, which is increased by the anterior chamber puncture.

As will be seen from the data shown in FIGS. 1 and 2, etodolac inhibited the increase in the $PGE_2$ content and the protein content present in the aqueous humor, due to the anterior chamber puncture.

In addition, meloxicam inhibited increases of the protein and $PGE_2$ contents in a concentration ranging from 0.1 to 1.0% and the inhibitory effect thereof was found to be conspicuous as compared with other drugs.

Table 1: Effect of Meloxicam on the Increase of Protein Content and $PGE_2$ Content after the Anterior Chamber Puncture

TABLE 1

|  | Control | Meloxicam | | |
|---|---|---|---|---|
|  |  | 0.1% | 0.5% | 1.0% |
| Protein Content (mg/ml) | 22.9 ± 1.0 | 16.2 ± 1.9** | 11.0 ± 1.5*** | 12.0 ± 2.1*** |
| Inhibition Rate |  | 29.3% | 52.2% | 47.6% |
| $PGE_2$ Content (pg/ml) | 2717.4 ± 506.8 | 680.6 ± 239.9* | 253.5 ± 67.0*** | 158.3 ± 30.0*** |
| Inhibition Rate |  | 75.0% | 90.7% | 94.2% |

Each value in this Table is an average of 11 to 12 eyes.
*,, *: $P < 0.05, 0.01, 0.001$: Dunnett's Test Test Example 2

Influence of Drugs on Uveitis Induced by LPS

In this Test Example, groups of Japanese white male rabbits each having a body weight ranging from 1.7 to 2.4 kg were used, wherein each group consisted of 12 to 16 eyes.

The lipopolysaccharide (LPS) (055: B5 type, available from Sigma Company) derived from *E. coli* was administered to these rabbits through the auricular veins in a dose of 1.25 μg/kg to thus induce uveitis. After 4 hours from the administration of LPS, the rabbits were killed by anesthetization with an excess of pentobarbital sodium (available from Tokyo Chemical Industry Co., Ltd.) and the anterior chamber fluid was collected.

The $PGE_2$ concentration and the amount of proteins present in the collected aqueous humor were determined according to the same methods used in Example 1.

In this respect, each test substance was dropped in the both eyes of these animals prior to one hour from the administration of LPS at a dose of about 60 μL/eye.

NS-398 as a test substance was dissolved or suspended in castor oil specified in the pharmacopoeia to concentrations of 0.5% and 5%. Meloxicam was diluted with physiological saline prior to use.

As will be clear from the data shown in the following Table 2, NS-398 considerably inhibited the increase in the amount of $PGE_2$. In addition, as will be clear from the data listed in the following Table 3, meloxicam inhibited increases of the protein and $PGE_2$ contents in a concentration ranging from 0.1 to 1.0% and thus, it was found to have an excellent anti-inflammatory effect.

TABLE 2

Effect of NS-398 on Uveitis Induced by LPS

|  | Control | NS-398 | |
|---|---|---|---|
|  |  | 0.5% | 5.0% |
| $PGE_2$ Content (pg/ml) | 1336.3 ± 380.1 | 4553 ± 118.6## | 542.8 ± 79.8# |
| Inhibition Rate |  | 65.9% | 59.4% |

Each value in this Table is an average of 12 to 16 eyes.
, ##: $P < 0.05, 0.01$: Dunnett's Test Table 3: Effect of Meloxicam on Uveitis Induced by LPS

TABLE 3

Effect of Meloxicam on Uveitis Induced by LPS

|  | Control | Meloxicam | | |
|---|---|---|---|---|
|  |  | 0.1% | 0.5% | 1.0% |
| Protein Content (mg/ml) | 24.2 ± 0.3 | 16.0 ± 1.9** | 14.3 ± 2.6** | 12.2 ± 1.8*** |
| Inhibition Rate |  | 33.8% | 40.8% | 49.4% |
| $PGE_2$ Content (pg/ml) | 2500.4± 647.3 | 1102.8 ± 139.4 | 780.9 ± 189.4** | 922.8 ± 291.2** |
| Inhibition Rate |  | 55.9% | 68.8% | 63.1% |

Each value in this Table is an average of 12 eyes.
, *: $P < 0.01, 0.001$: Dunnett's Test Test Example 3

Influence of Cyclooxygenase-Inhibitory Agent on Corneal Epithelial Cells and Conjunctival Cells Cells Used There were used SV40 immortalized human corneal epithelial cell strains (Araki-Sasaki et al., IOVS, 1995, 36:614-621) as the corneal cells and Chang human conjunctival cell strains (ATCC CCL-20.2) as the conjunctival cells.

Test Method

These cells were cultured in 96-well plate to a confluent of 30 to 50% and then each test substance stepwise diluted with the culture medium was added to the foregoing culture medium to thus carry out cultivation at 37° C. After completion of the cultivation, the plate was washed with PBS(−) and the number of residual cells was determined in terms of the β-hexosaminidase activity.

Method for Evaluating Toxicity

A group treated with only the solvent, which was used for dissolving the test substance was defined to be a negative control, the viable cell number observed for the control was assumed to be 100%, a dose-correlation curve was prepared on the basis of the viable cell number observed at each concentration of test substance and the concentration of each test substance required for achieving the survival rate of 50% (EC50) was determined from the curve and it was defined to be the toxicity value thereof.

As will be clear from the data listed in the following Table 4, etodolac which has relatively high selectivity for COX-2 shows low possibility of damaging cells such as corneal epithelial cells and conjunctival cells, as compared with compounds which have low selectivity for COX-1 and COX-2, such as indometacin or diclofenac sodium. This would lead to the development of a non-steroid anti-inflammatory agent, which hardly causes disorders of cornea.

In addition, the data shown in the following Table 5 indicate that meloxicam only quite weakly damages the corneal epithelial cells and conjunctival cells.

TABLE 4

Influence of Non-Steroid Anti-inflammatory Agents on Corneal Epithelial and Conjunctival Cells

|  | Corneal Epithelial Cells EC50 (mM) | Conjunctival Cells EC50 (mM) |
| --- | --- | --- |
| Diclofenac Sodium | 0.30 | 0.13 |
| Indometacin | 0.57 | 0.37 |
| Etodolac | 1.00 | 0.80 |

Note: The cells were exposed to each test substance for 24 hours.

TABLE 5

Influence of Non-Steroid Anti-inflammatory Agents on Corneal Epithelial and Conjunctival Cells

|  | Corneal Epithelial Cells EC50 (mM) | | Conjunctival Cells EC50 (mM) | |
| --- | --- | --- | --- | --- |
| Test Substance-Exposure Time (hr) | 24 | 48 | 24 | 48 |
| Meloxicam | 1.0< | 0.84 | 0.97 | 0.38 |
| Diclofenac Sodium | 0.63 | 0.23 | 0.23 | 0.22 |

INDUSTRIAL APPLICABILITY

The drug of the present invention, which can selectively inhibit COX-2, can be used in the form of an eye drop, which quite slightly damages the cornea and can show conspicuous effect in the treatment of ophthalmic inflammatory diseases. In particular, meloxicam has an excellent effect even when exposing it to the corneal epithelial cells over a long period of time as compared with the conjunctival cells.

What is claimed is:

1. A method for alleviating cell damage to the eye in a subject having an ophthalmic inflammatory disease or condition, comprising administering an eye drop comprising an effective amount of a drug that selectively inhibits cyclooxygenase-2 to said subject.

2. The method of claim 1, wherein said drug that selectively inhibits cyclooxygenase-2 is etodolac.

3. The method of claim 2, wherein the concentration of etodolac ranges from 0.5 to 5%.

4. The method of claim 1, wherein the drug that selectively inhibits cyclooxygenase-2 is N-(2-(cyclohexyloxy)-4-nitrophenyl) methane-sulfonamide (NS-398).

5. The method of claim 4, wherein the concentration of the N-(2-(cyclohexyloxy)-4-nitrophenyl)methane-sulfonamide (NS-398) ranges from 0.5% to 5%.

6. The method of claim 1, wherein the drug the selectively inhibits cyclooxygease-2 is meloxicam.

7. The method of claim 6, wherein the concentration of meloxicam ranges from 0.1% to 1%.

* * * * *